Figure 1:
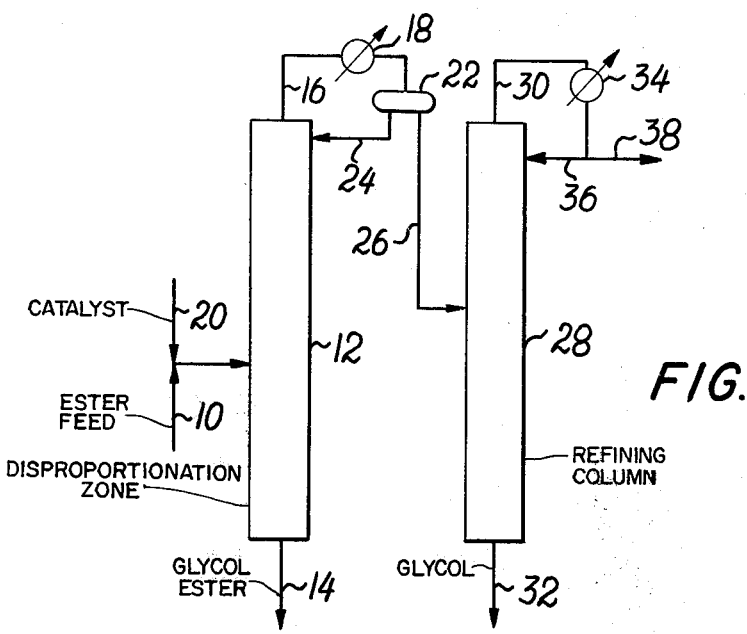

United States Patent [19]
Kollar

[11] 3,968,175
[45] July 6, 1976

[54] METHOD OF PRODUCING POLYHYDRIC COMPOUNDS

[75] Inventor: John Kollar, Wyckoff, N.J.

[73] Assignee: Halcon International, Inc., New York, N.Y.

[22] Filed: Nov. 29, 1974

[21] Appl. No.: 528,102

Related U.S. Application Data

[62] Division of Ser. No. 178,588, Sept. 8, 1971, Pat. No. 3,859,368.

[52] U.S. Cl............................................. 260/635 R
[51] Int. Cl.²...................................... C07C 29/00
[58] Field of Search.............. 260/635 R, 637 R, 491

[56] References Cited
UNITED STATES PATENTS

| | | | |
|---|---|---|---|
| 1,454,604 | 5/1923 | Rodebush | 260/635 R |
| 2,081,322 | 5/1937 | Carney | 260/638 R |
| 2,476,052 | 7/1949 | Lippincott | 260/491 |
| 2,776,323 | 1/1957 | Toland et al. | 260/635 R |
| 3,012,064 | 12/1961 | Hertling et al. | 260/491 |
| 3,098,093 | 7/1963 | Hagemeyer et al. | 260/638 R |
| 3,239,572 | 3/1966 | Zinstag | 260/638 R |
| 3,408,388 | 10/1968 | Hagemeyer et al. | 260/638 R |
| 3,651,102 | 3/1972 | Coopersmith | 260/635 R |
| 3,668,239 | 6/1972 | Kollar | 260/491 |

OTHER PUBLICATIONS

Horsley et al., 'Azeotropic Data," (1952) pp. 64 to 68.
Lange, "Handbook of Chemistry," 10th ed. (1961), pp. 564, 565.

*Primary Examiner*—Joseph E. Evans
*Attorney, Agent, or Firm*—William C. Long; David Dick; Riggs T. Stewart

[57] ABSTRACT

A polyhydric compound is produced by catalytically disproportionating a precursor which is a lower carboxylate ester of said compound containing at least one lower carboxylate group and at least one free hydroxyl group. Most preferably the invention relates to the production of a diol by the catalytic disproportionation of a lower carboxylate diester of the diol.

4 Claims, 2 Drawing Figures

METHOD OF PRODUCING POLYHYDRIC COMPOUNDS

This is a division of application Ser. No. 178,588, filed Sept. 8, 1971, now U.S. Pat. No. 3,859,368.

This invention relates to the treatment of lower carboxylate esters of polyhydric compounds, especially diols and triols, wherein the esters contain at least one lower carboxylate group and at least one free hydroxyl group, and is more particularly concerned with the preparation of diols, especially ethylene glycol, by catalytic disproportionation of lower carboxylate monoesters of such diols.

Diols and triols are known compounds, many of which are produced commercially in substantial quantities. Thus, ethylene glycol, for example, is a chemical of acknowledged commercial importance which is used primarily in the preparation of anti-freeze compositions and in the manufacture of polyester fibers. Ethylene glycol manufacturing processes of commercial interest have generally been based upon the use of ethylene oxide as a raw material. Recently, however, processes have been developed which make it possible to produce diols such as ethylene glycol and propylene glycol without the necessity for the intermediate manufacture of the oxide. These processes employ the liquid phase reaction of the appropriate olefin, a carboxylic acid, and molecular oxygen in the presence of a catalyst to produce carboxylic acid esters of the glycol. A process of this type is disclosed in Belgian Pat. No. 738,104. The glycol can be liberated by hydrolysis of the carboxylate esters produced in such processes. However, the hydrolysis reaction presents certain problems from the standpoint of efficiency and maximum conversion to the desired glycol. Related problems arise in connection with the production of other polyhydric compounds.

It is an object of this invention to provide an improved process for the production of a polyhydric compound from a precursor which is a lower carboxylate ester of the polyhydric compound and contains at least one lower carboxylate group and at least one free hydroxyl group.

It is another object of the invention to provide a process of the character indicated which can be combined with the preparation of ethylene glycol by the hydrolysis of lower carboxylate esters of ethylene glycol.

It is an additional object of the invention to provide a process which can be used to produce additional amounts of ethylene glycol from the partial hydrolyzation of lower carboxylate esters of ethylene glycol.

Other objects of the invention will be apparent from the following description of the invention and of illustrative embodiments thereof.

In accordance with the invention, lower carboxylate esters of dihydric and tridhydric alcohols, i.e. diols and triols, containing 2 to 6 carbon atoms, which esters contain at least one lower carboxylate ester group and at least one free hydroxyl group, especially lower carboxylate monoesters, are heated in the presence of a catalyst which can be generally characterized as a weak base. It has been discovered that in this environment the lower carboxylate ester undergoes, without the need for the presence of an extraneous reactant, what may be characterized as a disproportionation reaction to produce the free polyhydric alcohol, e.g. ethylene glycol, and the corresponding lower carboxylate ester of the polyhydric alcohol which has an added lower carboxylate group, e.g. the lower carboxylate ester of ethylene glycol, as illustrated in the following equations:

2 diol monoester → diol + diol diester

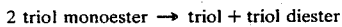

2 triol monoester → triol + triol diester

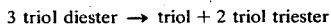

3 triol diester → triol + 2 triol triester

Esters which may be treated in accordance with the invention to produce the corresponding free polyhydric alcohols are the lower carboxylate ester of diols or triols which are the hydroxy derivatives of saturated acyclic or cyclic hydrocarbons or unsaturated acyclic or cyclic hydrocarbons. As indicated, the hydrocarbon radical of such diols or triols may contain 2 to 6 carbon atoms, preferably 2 to 4 carbon atoms in the case of acyclic compounds, and 6 carbon atoms in the case of cyclic compounds. Examples of such esters are the lower carboxylate monoesters of diols such as ethylene glycol, 1,2-propane diol (propylene glycol), 1,3-propane diol, 1,4-butane diol, 1,2-butane diol, 1,2-cyclohexane diol, 1,4-butene diol, 1,2-butene diol, catechol (1,2-benzenediol), resorcinol (1,3-benzenediol), and hydroquinone (1,4-benzenediol), and the lower carboxylate mono- and diesters of triols such as glycerol and 1,2,3-trihydroxy butane.

In the following discussion of the invention, the process will be described and exemplified with particular reference to esters of ethylene glycol, especially ethylene glycol monoacetate, but the process is equally applicable to esters of other diols and triols as defined above, the discussion in terms of esters of ethylene glycol being solely for convenience and ease of description. It is known that ethylene glycol carboxylate monoesters will undergo hydrolysis in the presence of water and in the presence of an acidic catalyst to produce ethylene glycol and the corresponding carboxylic acid, as disclosed, for example, in Belgian Pat. No. 738,104, and it is also known that in the presence of ethanol or methanol, ethylene glycol esters will react with the alcohol to produce ethylene glycol along with an ester of the alcohol, as disclosed, for example, in U.S. Pat. No. 1,454,604. The disproportionation of this invention, however, is different from such processes and, indeed, the process of the invention can be applied to the products of these prior processes in order to produce additional quantities of ethylene glycol.

The lower carboxylate ester which is treated in accordance with this invention is an ester of the appropriate diol or triol and an alkanoic acid having from 1 to 6 carbon atoms per molecule, such as formic acid, acetic acid, propionic acid, butyric acid, isobutyric acid, and the valeric and the caproic acids, the ester being a monoester in the case of diols, and a monoester or a diester in the case of triols. Accordingly, the lower carboxylate monoesters of ethylene glycol to which the process of this invention is applicable include ethylene glycol monoformate, ethylene glycol monoacetate, ethylene glycol monoproprionate, ethylene glycol monobutyrate, ethylene glycol monoisobutyrate, the ethylene glycol monovalerates and the ethylene glycol monocaproates. Ethylene glycol monoformate, ethylene glycol monoacetate, monopropionate, monobutyrate and monoisobutyrate, and mixtures of such monoesters with the corresponding diester, are especially desirable feedstocks, and the monoacetate and the diacetate-monoacetate mixtures are the preferred feedstocks. Of course, mixtures of esters such as mixtures of ethylene glycol monoacetate and ethylene glycol monopropionate, as well as mixtures with one or more diesters, including mixed diesters such as ethylene glycol acetate propionate, also can be employed. As used herein, therefore, the term "ester feed" is intended to include not only the lower carboxylate ethylene glycol monoester alone but also mixtures with the corresponding diester, and mixed esters, as well as mixtures of different ethylene glycol carboxylate esters. In general, mixtures of the monoester with a diester may contain varying amounts of the corresponding lower carboxylate diester of ethylene glycol, e.g. up to about 85 mol percent of the diester or diesters, based on the combined monoester-diester content of the mixture. Aside from the mono- and diesters, small amounts of by-products associated with the preparation of the glycol ester may also be present. Such by-products would normally include small quantities of ethylene glycol itself, water and acids, as well as unreacted lower carboxylic acid. They may also include catalyst residues and aldehydic by-products, such as, for example, acetaldehyde and formaldehyde. Thus, the effluent from the reaction wherein the monoester is produced can be processed as such in the disproportionation reaction of this invention. Typical reaction effluents of this nature are described, for example, in the above-mentioned Belgian Pat. No. 738,104, wherein the monoester is produced in the presence of substantial quantities of the diester, and in British Pat. No. 1,124,862, wherein the production of monoester substantially free from diester is disclosed. This invention, however, is applicable to glycol esters produced in any manner, whether by the process of the Belgian patent or the British patent or by various other processes. Further, the ester feed may comprise the effluent from the hydrolysis of ethylene glycol lower carboxylate esters, since even when only lower carboxylate diesters of ethylene glycol are hydrolyzed, the monoesters are formed during the course of the hydrolysis. It is generally preferable to purify such reaction and hydrolysis effluents to remove low-boiling materials, such as water and carboxylic acid, prior to subjecting the glycol ester to disproportionation. The invention is thus in no way limited to feeds comprising ethylene glycol monoesters from any particular source. In like manner, the invention is applicable to the corresponding lower carboxylate esters and ester mixtures of other diols and of triols of the character indicated above.

To provide the catalyst suitable for use in the disproportionation reaction of the invention there is used a compound which is a weak base in itself, or a substance which forms a weak base in situ in the presence of ethylene glycol carboxylate esters. For example, there may be used:

a. Metals and metal compounds, such as lithium, sodium, potassium, calcium, beryllium, magnesium, zinc, cadmium, strontium, aluminum, lead, chromium, molybdenum, manganese, iron, cobalt, germanium, nickel, copper, mercury, tin, boron, antimony, bismuth, and cerium as the metal, or as an oxide, hydride, carboxylate such as formate or acetate, alcoholate, or glycolate, or metal alkyl, for example tetrabutyl tin, cadmium acetate, lead acetate, zinc acetate, and dibutyl tin diacetate.

b. Tertiary amines, such as trimethyl amine, triethylene diamine, and dimethyl stearyl amine;

c. Quaternary ammonium salts of weak acids, such as tetramethyl ammonium acetate.

The preferred type of catalyst is that of group a) above, and the preferred individual catalysts are carboxylates of tin, lead, zinc, magnesium and cadmium, especially the acetates.

The amount of catalyst employed can vary, so long as there is an amount effective to cause the reaction to proceed. A generally suitable quantity is from 0.001 to 5.0% by weight based upon the free-hydroxyl-group-containing ester in the ester feed to the disproportionation zone. Preferably, the amount of catalyst is 0.01 to 1.0% and a particularly preferred quantity is 0.1 to 0.5%. Greater quantities can be used, the maximum amount being generally limited by economic considerations. The catalyst, if desired, can be added directly to the disproportionation zone, but the catalyst is preferably added to the ester feed prior to its introduction into the disproportionation zone. The residence time of the reactants in the disproportionation zone can also vary and, since increased residence times favor increased conversion of the ester to the polyhydric compound, a residence time sufficient to effect a reasonable conversion should be employed, e.g. at least about 0.25 minutes and, in general, the maximum residence time is governed only by the economics of the system. Preferably, however, a residence time of at least 2 minutes should be employed and, as a general rule, residence times longer than 50 minutes are not particularly useful.

While the disproportionation reaction will take place at ambient temperature, e.g. room temperature, the reaction is favored by heat and it is preferred, therefore, that the reaction be carried out at a temperature of at least about 100°C. In any case, the temperature should be above the melting points of the polyhydric compound and ester components of the reaction system. Ordinarily, temperatures greater than 280°C. are not necessary although higher temperatures can be employed if desired.

Pressure is not a parameter of the reaction and atmospheric, subatmospheric and superatmospheric pressures may be employed as desired. Obviously minimum and maximum pressure will be related to the type of apparatus available and as a general rule there is not particular advantage in operation at pressures less than 50 mm. Hg or greater than 250 psig.

The polyhydric compound thus produced is separated from the reaction mixture in any convenient manner, as by extraction with a selective solvent or by distillation, e.g. extractive distillation or, especially in the case of ethylene glycol and propylene glycol, use may be made of azeotropic distillation as described in the co-pending application of Richard L. Golden entitled "Recovery of Alkylene Glycols" and filed on even date herewith and now U.S. Pat. No. 3,809,724. In the case of solvent extraction or extractive distillation there is suitably used a high-boiling compound which is inert with respect to the reaction mixture, such as a hydrocarbon or other non-polar or mildly-polar material such as an ether. The extracting solvent will be liquid under the prevailing conditions and will most suitably have a boiling point which is 50°C. or higher than the boiling point of the dicarboxylate, e.g. ethylene glycol diacetate, in the reaction mixture. A typically suitable hydrocarbon is dodecane, and a typical extracting ether is diphenyl ether. The disproportionation and the separation of the product diol or triol can be carried out individually in different zones but one of the important advantages of this invention is that the disproportionation reaction can be effected simultaneously with the separation operation. Thus, the disproportionation reaction can be effected continuously in a distillation or extraction zone, e.g. a fractional distillation column, with continuous introduction of ester feed and continuous removal of product diol or triol as it is produced. The concurrent extraction or distillation taking place in the disproportionation zone has the effect not only of providing for the recovery of the desired polyhydric compound from the reaction mixture but, as will be apparent from the equation referred to above, such removal of polyhydric compound favors the reaction itself. Thus when azeotropic distillation is employed as described in co-pending application, and this is of particular use in the case of ethylene glycol and propylene glycol, any azeotroping agent which will form a minimum-boiling azeotrope with the polyhydric compound and which can be separated by fractional distillation from any other azeotrope which may be formed, and from other components of the system, and which is essentially water-immiscible, can be used and this embodiment, therefore, is not limited to any particular agent but it is preferred, from the standpoint of ease of operation, to employ an azeotroping agent which forms a minimum-boiling azeotrope with the polyhydric compound and which has a boiling point at atmospheric pressure of 135° to 190°C., preferably 150° to 170°C. When the mixture undergoing disproportionation is concurrently distilled in the presence of azeotroping agents such as agents of the character indicated, the resulting polyhydric compound azeotrope with the azeotroping agent can readily be removed from the system by distillation and the polyhydric compound can be readily recovered. The azeotrope, when condensed, separates into two phases, viz. a phase composed essentially of the azeotroping agent and a phase containing the polyhydric compound. The phase containing the azeotroping agent is readily separated, as by decantation, from the polyhydric compound-containing phase and is returned to the distillation zone, i.e. the zone in which the disproportionation reaction is taking place under distillation conditions, as reflux. Consequently, the azeotroping agent is merely recirculated in the system and the originally-supplied quantity of azeotroping agent is continuously available for reuse.

Suitably the azeotroping agent has a boiling point within the aboveindicated 135° to 190°C. range at atmospheric pressure, most advantageously within the specified preferred temperature range, but it preferably also forms a minimum-boiling azeotrope which has a boiling point which differs by at least 5°C. from the boiling point at the same pressure of the azeotropes formed by the polyhydric compound with any of the carboxylate esters of the polyhydric compound present in the mixture. Particularly suitable as azeotroping agents are the saturated hydrocarbons, both acyclic and cyclic, having boiling points within the specified range, the aromatic hydrocarbons, and those which have the required boiling points at atmospheric pressure within the range of 135° to 190°C. are, for the most part, alkyl-substituted benzenes, halogenated hydrocarbons, especially halogenated aromatic hydrocarbons, ethers, ketones and alcohols, and an especially preferred azeotroping agent is pseudocumene. As disclosed in said co-pending application, agents of this character include the following (Table A); wherein the boiling points of the ethylene glycol azeotropes are indicated.

TABLE A

| Azeotroping Agent | Azeotrope b.p., °C. 760 mm.Hg | Agent b.p., °C. 760 mm.Hg |
|---|---|---|
| Ethylbenzene | 133 | 136.2 |
| Cumene | 147 | 152.8 |
| Anisole | 150.5 | 153.9 |
| Bromobenzene | 150.2 | 156 |
| 1-Bromohexane | 150.5 | 156 |
| 1,2,3-Trichloropropane | 150.8 | 156.9 |
| Propylbenzene | 152 | 159 |
| o-Chlorotoluene | 152.5 | 159 |
| 2,7-Dimethyl Octane | 153 | 160 |
| p-Chlorotoluene | 155 | 162 |
| Mesitylene | 156 | 164.6 |
| 1,3-Dibromopropane | 160.2 | 167.3 |
| 2,6-Dimethyl-4-Heptanone | 164.2 | 168 |
| Pseudocumene | 158 | 169.5 |
| Phenetole | 161.5 | 172 |
| m-Dichlorobenzene | 166 | 172 |
| 2-Octanone | 168 | 172.9 |
| Benzylmethyl Ether | 159.8 | 174 |
| Decane | 161 | 174 |
| p-Dichlorobenzene | 163 | 174 |
| Heptyl Alcohol | 174.1 | 177 |
| p-Cymene | 163.2 | 177 |
| p-Methylanisole | 166.6 | 177 |
| bis-(2-chloroethyl)ether | 171 | 178 |
| o-Dichlorobenzene | 165.8 | 179 |

As disclosed in said co-pending application, some typical agents which form minimum boiling azeotropes with propylene glycol include o-xylene (azeo. b.p. 135.8°C.), dibutyl ether (azeo. b.p. 136°C.) and 2-octanone (azeo. b.p. 169°C.).

The polyhydric compound containing phase from the azeotropic condensate is subjected to further distillation to remove as overhead the ethylene glycol monocarboxylate ester and a relatively small amount of the polyhydric compound, along with any azeotroping agent which may be present, and substantially pure ethylene glycol is withdrawn as bottoms product. The glycol-rich phase from the extractive distillation can be similarly treated. The overhead product from this last-mentioned distillation step is advantageously combined with the feed to the distillation column.

As previously mentioned, the ester disproportionation process of this invention is particularly adapted to be integrated with the hydrolysis of lower carboxylate esters of the polyhydric compound, e.g. ethylene glycol lower carboxylate monoesters, diesters and mixtures of monoesters and diesters, i.e. it can follow the hydrolysis operation in order to produce additional quantities of polyhydric compound. Thus, illustrating the hydrolysis operation by the case of ethylene glycol, which is representative of the other polyhydric compounds within the scope of the invention, not only can the ester feed to the disproportionation reaction consist essentially of ethylene glycol lower carboxylate monoester alone or in admixture with ethylene glycol lower carboxylate diester along with minimum amounts of other materials which may be present as a result of the manufacturing process by means of which the esters are produced but the ester feed may also comprise the effluent from the partial hydrolysis of ethylene glycol carboxylate esters, suitably after removal of water and carboxylic acid, which effluent will contain not only the ethylene glycol monoester and generally the ethylene glycol diester, but will also contain varying amounts of ethylene glycol itself. The hydrolysis of ethylene glycol esters is an equilibrium reaction and to obtain high ester conversion would conventionally require the use of large excesses of water. thereby sharply reducing the concentration of the reaction mixture and complicating recovery procedures. It is advantageous, therefore, unless special hydrolysis techniques are employed, to limit the conversion of the ester to about 80 mol %, i.e. to effect only a partial hydrolysis to this extent. Such hydrolysis can be effected with reasonable quantities of water. The process of this invention makes it possible to increase the ester conversion and thus to produce additional quantities of ethylene glycol without problems of increasing conversion in the hydrolysis reaction itself. This is particularly the case when, in accordance with the preferred embodiment of this invention, the disproportionation is carried out simultaneously with azeotropic distillation. By this means, not only is removal of the ethylene glycol which is formed as a result of the disproportionation reaction effected, but the ethylene glycol contained in the ester feed to the disproportionation zone is also effectively recovered, so that an integrated system for producing ethylene glycol from its lower carboxylate esters in an efficient manner is provided.

The feed to the hydrolysis operation can be the previously-described "ester feed" or it can consist essentially of the monoester, or of the diester, or of mixtures of mono- and diesters in any proportion. In general, the reaction continues until an equilibrium mixture comprising diester, monoester, ethylene glycol, carboxylic acid and water is formed. Before feeding the hydrolysis reaction product to the disproportionation reaction, the water and carboxylic acid are preferably removed from the hydrolysis effluent, e.g. by distillation in any convenient manner, these two compounds being readily separated from the ethylene glycol and the lower carboxylic esters. In effecting the hydrolysis, the ethylene glycol lower carboxylate ester, or ester mixture, is suitably heated in the presence of water until at least some hydrolysis has occurred. Although the hydrolysis reaction will take place solely under the influence of heat, it is preferred, in order to increase the rate of reaction, to effect hydrolysis in the presence of an acidic ester hydrolysis catalyst, most preferably a solid catalyst, e.g. in the form of an acidic ion exchange resin, is employed. The hydrolysis step is thus suitably carried out by causing the glycol ester or ester mixture to react under the influence of heat (with or without a catalyst) to liberate (i.e. hydrolyze) from 15 to 80 mol % of the acyl moieties, e.g. acetate moieties, as lower carboxylic acid, e.g. acetic acid. At the same time, ethylene glycol is liberated.

In the hydrolysis reaction it is desirable to use at least .25 mol of water per equivalent of acyl moiety present in the hydrolysis feed. Preferably the amount of water added is in the range of from about 0.75 to 5 mols of water per equivalent of acyl moiety in the hydrolysis feed. Of course, greater amounts of water can be used, for example up to 20 mols per equivalent of acyl moiety in the hydrolysis feed, but the use of such large amounts of water is both unnecessary and economically disadvantageous. It is a feature of this invention that the combination of a disproportionation operation with the hydrolysis operation makes it possible to operate the hydrolysis reaction efficiently and effectively by using only limited amounts of water since only partial hydrolysis is necessary.

Hydrolysis reaction temperatures of at least about 50°C. are necessary in order to obtain economically satisfactory rates of hydrolysis except that, when catalysts are employed, temperatures as low as 25°C. can be satisfactorily used. It is generally not desirable to employ the hydrolysis reaction temperatures above about 250°C., however, since at higher temperatures thermal degradation, with concomitant formation of color bodies, can become significant. Preferably temperatures of about 50°C. to about 200°C. are employed. Pressure is not, in any manner, critical to the conduct of the hydrolysis and the pressure values given above in connection with the disproportionation reaction are suitable as long as they are sufficient at the prevailing temperature to keep the reaction mixture in the liquid phase. Thus pressures of as little as 50 mm. Hg can be employed as also can pressures of several thousand psia. Residence time of reactants and products within the hydrolysis zone is in no way critical as long as the reaction proceeds reasonably near to equilibrium. Thus, for example, residence times from as little as 1 minute up to and including several hours, e.g. 4 hours, or longer are entirely feasible.

While any conventional ester hydrolysis catalyst can be used, for example, materials such as the mineral acids, e.g. hydrochloric, sulfuric and phosphoric acids, and also include organic acids such as oxalic, tartaric and malic acids, as well as such materials as trichloracetic acid and the aryl sulfonic acids, e.g., p-toluene sulfonic acid, it is necessary to separate the catalyst from the hydrolysis effluent, e.g. by distilling the rest of the effluent away from the less volatile catalyst, or by chemical treatment to inactivate or remove the hydrolysis catalyst, before further processing. When such catalysts are used, however, they are suitably employed in relatively small amounts, e.g. quantities of as little as 0.0001 mol per equivalent of acyl moiety in the feed to the hydrolysis zone being suitable. Larger proportions can be employed though there is little practical reason to employ amounts greater than about 0.001 mol of acid per equivalent of glycol moiety in the feed. It is most preferred, therefore, to use solid catalysts such as acidic ion exchange resins or molecular sieves, e.g. metal alumina silicates (siliceous zeolites) such as molecular sieves of the "A" and "X" series, e.g. "Molecular Sieve 4A," and other acidic heterogeneous solid catalysts which can be used in the form of beds through which the feed to be hydrolyzed can be continuously passed, so that no separation step is necessary. Typical examples of suitable ion exchange resins include cationic exchange resins of the sulfonic acid type, such as the polystyrene sulfonic acids, exemplified by commercial products sold under the names Dowex-50, Duolite C-20, and Ionac Z40.

Following the hydrolysis reaction, the hydrolyzate, which contains carboxylic acid, e.g. acetic acid, and water, in addition to ethylene glycol, monoesters, and diesters is, as mentioned, suitably passed into a distillation column wherein a major portion of the carboxylic acid and water is vaporized and removed as overhead for subsequent recovery. This separation can be carried out in any conventional distillation column. In general, it is desirable to separate at least 99 percent of the water and carboxylic acid present in the mixture before proceeding with the removal and recovery of the ethylene glycol. Although, as mentioned, the distillation step to separate water and carboxylic acid can be carried out over a wide range of conditions, it has been found preferable to operate at pot temperatures of 170° to 240°C. and at pressures of from 400 mm.Hg to 50 psig. It will be understood that the water and carboxylic acid can be removed in a single distillation operation or the distillation may be carried out in two distillation zones in series with the water and some of the carboxylic acid being removed in the first distillation zone and the remainder of the carboxylic acid to be removed being separated in the second distillation zone. This distillation step is suitably carried out in conventional manner and the selection of specific conditions for treatment of specific feeds to separate specific amounts of water and carboxylic acid will be readily apparent to persons skilled in the art.

Figure 2:
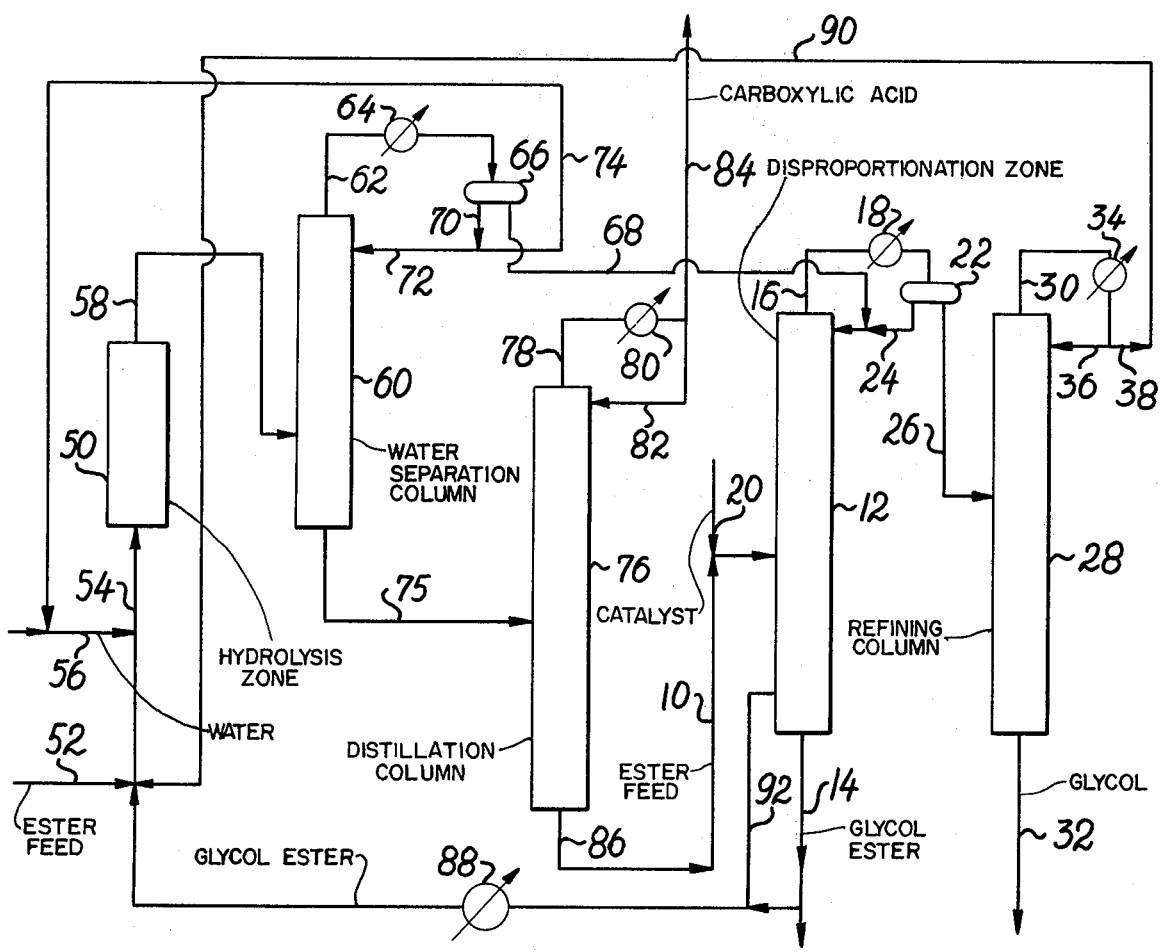

The invention will be more fully understood by reference to the accompanying drawing, wherein:

FIG. 1 is a diagrammatic view of a system for carrying out the disproportionation reaction of the invention simultaneously with removal by distillation of the produced polyhydric compound, illustrated by ethylene glycol, and FIG. 2 is a similar diagrammatic view of an overall system wherein the disproportionation reaction is integrated with ester hydrolysis, illustrated by ethylene glycol esters.

Referring to the drawing, and more particularly to FIG. 1, an ester feed stream comprising lower carboxylate monoester of ethylene glycol is fed through line 10 to disproportionation zone 12 which, in the embodiment illustrated, is a distillation column suitably provided with heating means, e.g. a conventional reboiler or the like (not shown) and with a bottoms withdrawal line 14 and an overhead vapor line 16, the latter being connected to a condenser 18. The catalyst is introduced through line 20 so that it may be admixed with the ester feed prior to its introduction into the disproportionation zone. The ethylene glycol produced in the disproportionation reaction which takes place in column 12 is removed through line 16, suitably in the form of an azeotrope with an azeotroping agent, and glycol ester is withdrawn through line 14. The overhead vapor from column 12 leaves through line 16 and is condensed in condenser 18, flows to a phase-separator 22, and the condensed azeotroping agent is returned to column 12 through line 24 as reflux, whereas the ethylene glycol phase is withdrawn through line 26 and is introduced into a refning column 28, also provided with any suitable heating means (not shown) wherein ethylene glycol ester and azeotroping agent contained in the ethylene glycol phase withdrawn from phase separator 22 is removed as vapor through line 30, and ethylene glycol in substantially purified form is withdrawn as bottoms through line 32. The vapors in line 30 are condensed in condenser 34 and a portion is returned as reflux to column 28 through line 36 and the remainder is withdrawn through line 38. Some or all of the material in line 38 may be combined with the feed to column 12, and make-up azeotroping agent, as required, is also suitably added through line 10 or through line 20.

Referring now to FIG. 2, wherein the disproportionation-azeotropic distillation system just described is integrated with the hydrolysis of lower carboxylic esters of ethylene glycol to provide the feed to disproportionation column 12, a hydrolysis ester feed stream enters a hydrolysis zone 50 through line 52 and line 54 and water for the hydrolysis enters through line 56 and is combined with the hydrolysis ester feed in line 54 before entering zone 50. Zone 50 is suitably filled with a bed of solid hydrolysis catalyst, e.g. a bed of acidic ion exchange resin, and the combined water and ester feed stream flows upwardly through the bed, and the partially-hydrolyzed reaction product is removed through line 58. The product stream in line 58 is introduced into a water separation column 60, provided wih a reboiler or other heating means (not shown) wherein water is vaporized and, along with a small amount of carboxylic acid, is withdrawn through line 62 and condensed in condenser 64. Since in the embodiment illustrated in FIG. 2, the condensate from condenser 64 will contain some azeotroping agent, as will be explained below, the condensate passes to a phase separator 66 wherein the water and carboxylic acid form one phase and the azeotroping agent forms a second phase, the latter being withdrawn from separator 66 through line 68. The aqueous phase is withdrawn through line 70, with part of it being returned to column 60 through line 72 as reflux and the remainder being recycled to column 50 through line 74 which empties into water supply line 56. The portion of the hydrolysis product stream supplied to column 60 which is not vaporized and withdrawn through line 62 and which comprises ethylene glycol, carboxylic acid and lower carboxylic esters of ethylene glycol is withdrawn through line 75 and fed to a distillation column 76, also provided with appropriate heating means (not shown). In distillation column 76, the carboxylic acid is vaporized and carboxylic acid vapors are withdrawn through line 78 and condensed in condenser 80 with some of the condensate being returned to column 76 as reflux through line 82 and the remainder being withdrawn from the system through line 84. The carboxylic acid stream will also contain any water which was not separated in column 60. The essentially water-and carboxylic acid-free ethylene glycol-lower carboxylate ester mixture is withdrawn from distillation zone 76 through line 86 and is supplied to line 10 to provide the ester feed to disproportionation zone 12, as described above in connection with the discussion of FIG. 1. To complete the integration of the disproportionation system with the hydrolysis system, a line 90 connects with line 38 to conduct the withdrawn condensate containing azeotroping agent from column 28 to the feed to hydrolysis zone 50 and a side stream from column 12 comprising vapors of lower carboxylate esters of ethylene glycol is withdrawn through line 92 and also combined with the feed to the hydrolysis zone, after being condensed in condenser 88. A purge stream comprising liquid esters and catalyst is withdrawn through line 14 in order to remove the disproportionation catalyst. When the hydrolysis is carried out thermally, i.e. without the use of a hydrolysis catalyst, then the ester stream from the disproportionation zone to the hydrolysis zone can be a liquid stream, e.g. line 92 can be connected to line 14 and the disproportionation catalyst will recycle through the system. Should any of the disproportionation catalyst reach the ion exchange resin serving as hydrolysis catalyst, it will be retained by the resin which can then be suitably regenerated to remove the accumulated disproportionation catalyst or it can be replaced from time to time. Actually, the solid hydrolysis catalyst will eventually become contaminated with minor amounts of impurities which may be contained in the hydrolysis feed and will need to be regenerated in conventional manner, or replaced.

The following examples of specific application will serve to give a fuller understanding of the invention but it will be understood that these examples are illustrative only and are not intended as limiting the invention.

EXAMPLE I

A feed mixture composed of 47.2 wt. % ethylene glycol diacetate (EGDA), 46.25 wt. % ethylene glycol monoacetate (EGMA), 6.4 wt. % ethylene glycol (EG), and 0.15 wt. % of lead acetate is introduced into an Oldershaw distillation column consisting of 30 glass trays of 1 inch in diameter above the feed point and 20 trays of 1 inch in diameter below the feed point and provided with a 300 cc electrically-heated glass reboiler powered with a Variac set to maintain a constant temperature of 189°C. in the reboiler, and the mixture is distilled in the presence of o-chlorotoluene as azeotroping agent (AA). The overhead vapors (154°C.) are condensed in a sloping glass tube condenser, and the condensed two-phase liquid is decanted in a Dean-Stark tube. The heavier liquid comprising ethylene glycol and ester is drawn off periodically and the lighter liquid comprising the o-chlorotoluene is decanted through the overflow line and is pumped to the top tray of the column at a fixed flow rate.

During steady state operation 150 cc (approx. 165 g./hr.) of the feed mixture is introduced at the feed point and 170 cc/hr. of o-chlorotoluene is introduced on the top plate. Most of the AA supplied is reflux of the lighter liquid to which make-up AA is added to compensate for that passing into the withdrawn overhead phase. Each hour a total of about 31 g. overhead product and a total of about 138 g. of bottoms product are withdrawn from the column. The analyses of each product are as follows, expressed as wt. %:

|      | Overhead | Bottoms |
|------|----------|---------|
| EG   | 72.6     | 0.67    |
| EGMA | 21.8     | 23.8    |
| EGDA | <0.1     | 74.1    |
| AA   | 5.5      | 1.38    |

Material balance shows that 49.8 percent of the EGMA has been converted to EG and EGDA and that 63.5 percent of the theoretically attainable EG is in the overhead product. All of the catalyst is in the bottoms product and is excluded from the values given above.

EXAMPLE II

The procedure of Example I is repeated except that the feed contains 0.25 wt. % lead acetate, using a rate of 150 cc/hr. and an o-chlorotoluene feed of 195 cc/hr. The analyses of the overhead (about 36 g.) and bottoms (about 131 g.) products are as follows:

|      | Overhead | Bottoms |
|------|----------|---------|
| EG   | 71.3     | 0.31    |
| EGMA | 22.3     | 17.0    |
| EGDA | <0.1     | 82.6    |
| AA   | 5.72     | <0.1    |

Conversion of EGMA to ethylene glycol and EGDA is 60.7 percent and 73.4 percent of the theoretical ethylene glycol is in the overhead.

EXAMPLE III

Using the apparatus described in Example I, the feed mixture of Example I, but containing 0.50% lead acetate, was introduced at the rate of 150 cc/hr. and o-chlorotoluene is fed to the top plate at the rate of 145 cc/hr. Each hour a total of about 24 g. overhead product and a total of about 142 g. bottoms product are withdrawn, the analyses of these products, in wt. %, being as follows:

|      | Overhead | Bottoms |
|------|----------|---------|
| EG   | 87.8     | 0.37    |
| EGMA | 7.75     | 19.7    |
| EGDA | <0.1     | 79.8    |
| AA   | 3.25     | <0.1    |

Material balance shows that 58 percent of the EGMA has been converted to ethylene glycol and EGDA and that 75.4 percent of the theoretically attainable ethylene glycol is in the overhead product.

EXAMPLE IV

Using apparatus corresponding to that described in Example I, but having trays of 2 inches diameter, a feed mixture having the composition of that used in Example I but containing 0.25 wt. % lead acetate is introduced at the rate of 111 g./hr., and o-chlorotoluene is fed to the top plate at the rate of 130 cc/hr. Each hour a total of about 20 g. overhead product and a total of about 90 g. bottoms product are withdrawn from the column. The two products analyze as follows in wt. %:

|                 | Overhead | Bottoms |
|-----------------|----------|---------|
| EG              | 79.8     | 0.14    |
| EGMA            | 14.6     | 13.7    |
| EGDA            | <0.1     | 86.1    |
| o-chlorotoluene | 4.53     | <0.1    |

Material balance shows that 70.1 percent of the ethylene glycol monoacetate has been converted to ethylene glycol and EGDA and that 70.4 % of the theoretically attainable ethylene glycol is in the overhead product.

EXAMPLE V

Again using the apparatus corresponding to that described in Example I, but having trays of 2 inches diameter, a feed mixture composed of about 46.55 wt. % of EGDA, 47.05 wt. % of EGMA, 6.15 wt. % EG and 0.25 wt. % lead acetate is introduced at the rate of 150 g./hr., and o-chlorotoluene is fed to the top plate at the rate of 195 cc/hr. Each hour a total of about 31 g. overhead product and a total of about 135 g. bottoms product are withdrawn from the column. The two products analyze as follows, in wt. %:

|                 | Overhead | Bottoms |
|-----------------|----------|---------|
| EG              | 92.6     | 0.2     |
| EGMA            | 2.93     | 14.9    |
| EGDA            | <0.1     | 84.8    |
| o-chlorotoluene | 2.66     | <0.1    |

Material balance shows that 73 percent of the ethylene glycol monoacetate has been converted to ethylene glycol and EGDA and that 84.7 percent of the theoretically attainable ethylene glycol is in the overhead product.

removed from the disproportionation zone by azeotropic distillation with o-chlorotoluene and the composition of the feed is 48 wt. % EGDA, 46 wt. % EGMA, and 6 wt. % EG. The pertinent data are shown in Table B below.

TABLE B

| Example | Catalyst | Cat. Amt. % | Pot Temp. °C. | Feed cc./hr. | AA cc./hr. | Head Temp. °C. | Overhead g./hr. | Overhead Composition, Wt. % | | | | Bottoms Composition, Wt. % | | | | EGMA Conversion(%) |
|---|---|---|---|---|---|---|---|---|---|---|---|---|---|---|---|---|
| | | | | | | | | EG | EGMA | EGDA | AA | EG | EGMA | EGDA | AA | |
| VIII | TMAA | 0.15 | 189 | 150 | 195 | 151 | 28 | 70.3 | 21.2 | tr. | 8.4 | tr. | 27.1 | 72.9 | tr. | 45 |
| IX | ZA | 0.25 | 186 | 150 | 195 | 154 | 37 | 57 | 34.2 | tr. | 8.8 | 0.4 | 29.1 | 70.5 | tr. | 61.9 |
| X | TBT | 0.2 | 191 | 150 | 200 | 155 | 28 | 53.7 | 35.8 | tr. | 10.5 | tr. | 27.5 | 72.5 | tr. | 50.3 |
| XI | TBT | 1.5 | 190 | 150 | 200 | 156 | 32 | 58.9 | 35.2 | 0.3 | 5.6 | tr. | 25.6 | 74.4 | tr. | 54.1 |
| XII | DBTDA | 3 | 187 | 150 | 200 | 154 | 32 | 75.8 | 18.3 | tr. | 5.8 | tr. | 16.5 | 83.5 | tr. | 70 |
| XIII | CA | 0.15 | 191 | 150 | 195 | 155 | 34 | 63.6 | 29 | tr. | 7.3 | tr. | 20.3 | 79.7 | tr. | 64.6 |
| XIV | LA | 0.05 | 189 | 150 | 195 | 154 | 32 | 67 | 26.3 | tr. | 6.7 | tr. | 23.4 | 76.6 | tr. | 63.1 |
| XV* | LA | 0.15 | 185 | 150 | 140 | 160 | 34 | 70.9 | 24.4 | tr. | 2.6 | tr. | 15.4 | 84.5 | tr. | 58.2 |
| XVI* | LA | 0.05 | 189 | 150 | 140 | 162 | 29 | 78.7 | 18.6 | tr. | 2.7 | tr. | 16.9 | 83.1 | tr. | 61.7 |

TMAA = Trimethyl Ammonium Acetate
ZA = Zinc Acetate
TBT = Tetrabutyl Tin
DBTDA = Dibutyl Tin Diacetate
CA = Cadmium Acetate
LA = Lead Acetate
*Pseudocumene azeotroping agent; feed comprising (wt. %) 51.6 EGDA, 44.6 EGMA, 3.8 EG.

EXAMPLE VI

A feed consisting of ethylene glycol monoacetate containing 0.1 wt. % of lead acetate is reacted at 180°C. for 15 minutes in a nitrogen atmosphere under a pressure of 100 psig. At the end of this reaction period the product mixture is removed from the reaction zone and contains 5.6 wt. % ethylene glycol, 13.1 wt. % ethylene glycol diacetate, and 81.3 wt. % ethylene glycol monoacetate.

When either ethylene glycol or ethylene glycol diacetate is removed from the mixture, as by solvent extraction or distillation, and the remaining mixture is further reacted, additional amounts of ethylene glycol and ethylene glycol diacetate are formed by further disproportionation of the ethylene glycol monoacetate.

EXAMPLE VII

A feed consisting of 208 g. ethylene glycol monoacetate containing 0.25 wt. % zinc acetate, is introduced near the top of a countercurrent extraction column having 20 extraction stages and maintained at a temperature of 180°C. The feed is passed downwardly countercurrently to 600 g. of hexadecane introduced at the bottom of the column and the flow is at a rate to provide an average residence time of about 5 minutes per stage. The hexadecane phase which is removed from the top of the apparatus is composed of approximately 600 g. hexadecane and 130 g. ethylene glycol diacetate, whereas the ethylene glycol phase removed from the bottom of the apparatus amounts to 78 g. and is composed of 70.5 wt. % ethylene glycol and 29.5 wt. % ethylene glycol monoacetate.

When the processes of the foregoing examples are repeated with corresponding amounts of trimethyl ammonium acetate, zinc acetate, (lead acetate in the case of Example VII) tetrabutyl tin, dibutyl tin diacetate, cadium acetate, or trimethyl ammonium amine, as disproportionation catalyst, corresponding disproportionation of the monoester is achieved.

Examples VIII – XVI

Using the apparatus of Example I, a series of disproportionations are run using various catalysts. In each case, unless otherwise indicated, the ethylene glycol is

EXAMPLE XVII

A combined hydrolysis-disproportionation system as illustrated in FIG. 2 is used for continuously hydrolyzing an ester mixture containing some ethylene glycol and composed of approximately 54 mol % of ethylene glycol diacetate, 41 mol % of ethylene glycol monoacetate, and 5 mol % ethylene glycol, and subsequently disproportionating the ethylene glycol monoacetate and recovering ethylene glycol from the system. The following discussion relates to the operation of this system after steady state conditions are attained.

The fresh feed mixture is introduced through line 56 at a rate to provide, per hour, 244.7 lb. mols EGDA, 184.9 lb. mols EGMA, and 24.4 lb. mols EG, and this mixture is combined with recycle streams 90 and 92 to provide a flow of approximately 1088 lb. mols/hr. EGDA and 185 lb. mols/hr. EGMA, and 34.8 lb. mols/hr. EG, into hydrolysis zone 50, which is maintained at a temperature of 90°C. and consists of about an 800 cubic foot bed of 100 to 200 mesh Dowex 50W-X8 ion exchange resin. At the same time water is introduced at the rate of approximately 656.4 lb. mols/hr. make up water and approximately 530.9 lb. mols/hr. recycle water containing a small amount of acetic acid. The partially-hydrolyzed product (about 52 percent of the EGDA fed to the hydrolysis zone remains unconverted) is withdrawn through line 58 and passed to the 9th plate from the top of column 60 which contains 53 actual plates and is operated at a reboiler temperature of about 152°C. and at substantially atmospheric pressure, with a reflux ratio of 2:1 to separate as overhead the water-acetic acid recycle stream and a bottoms stream comprising the remainder of the hydrolysis effluent which is passed onto the 12th plate from the top of column 76 which has 28 actual plates and is operated at a reboiler temperature of 182°C. and at atmospheric pressure, with a reflux ratio of 1.6:1. Azeotroping agent in recycle stream 90 is removed in separator 66 and returned to column 12 through line 68. In column 76 the remainder of the acetic acid and water are separated and withdrawn through line 84. The bottoms product from column 76, comprising the ester and glycol components of the hydrolysis reaction, has added to it lead acetate at the rate of approximately 0.24 lb. mol/hr. and the mixture is introduced to the 20th plate from the top of the azeotropic distillation column 12 which contains 55 actual plates and employs o-chlorotoluene as azeotroping agent which is continuously recycled to the column through lines 24 and 68 and is present in an amount to provide a ratio of azeotroping agent to ester-glycol feed of approximately 1.9:1. All of the azeotroping agent condensed and separated in separator 22 is returned to column 12 and the ethylene glycol phase from separator 22, which contains approximately 4 mol % o-chlorotoluene, 19 mol % EGMA, and is free from EGDA, is fed to refining column 28 which contains 60 actual plates and is operated at a reboiler temperature of 173°C. and at a pressure of 200 mm.Hg with a reflux ratio of 7:1 and there is obtained a bottoms product consisting essentially of ethylene glycol, which is withdrawn at the rate of approximately 444 lb. mols/hr., and the net overhead, as previously mentioned, is recycled to the hydrolyzer through line 90. An ester purge stream of 9 lb. mols/hr. (calculated as ethylene glycol diacetate) and containing the catalyst is withdrawn through line 14 and can be processed for catalyst recovery, if desired and the catalyst recycled to line 20. A vapor stream composed substantially entirely of EGDA is withdrawn through line 92 from above the 53rd plate from the top of column 12 and, after condensation in condenser 88 provides the previously-mentioned recycle stream. In the foregoing example there was substantially 85–90 percent conversion of EGMA to EG and EGDA.

In the foregoing example, the hydrolysis feed contains ethylene glycol and a substantial amount of ethylene glycol monoester which is representative of a feed which would normally be available from the processing of a carboxylate ester product produced by the reaction of acetic acid and ethylene, but corresponding effective operation is also realized when this example is repeated with a feed containing essentially no ethylene glycol or lesser amounts of ethylene glycol monoacetate or composed essentially of ethylene glycol diacetate. Such feeds require appropriate adjustment in the operation of the distillation units as will be obvious to persons skilled in the art. Ethylene glycol which is recovered as the product of this process is of high-purity such that it can be used directly in the production of fiber-grade polyesters.

What has been said above with regard to the treatment of lower carboxylate esters of ethylene glycol and with respect to the production and recovery of ethylene glycol also applies, as previously indicated, to the treatment of lower carboxylate esters of other polyhydric compounds of the character specified above. Thus, when Example VI, for instance, is repeated using propylene glycol monoacetate, or the monoacetate of 1,4-butane diol, or the monoacetate of 1,2-butene diol, or the monoacetate of catechol, or the diacetate of glycerol, corresponding results are achieved and effective production of the free polyhydric compound is realized. In like manner, corresponding results are obtained when the esters of other lower alkanoic acids are used in place of the acetic acid esters, for example the formates and propionates. It is intended, therefore, that all matter contained in the foregoing description shall be interpreted as illustrative only and not as limitative of the invention.

I claim:

1. A process for producing an alkene diol containing 2 to 6 carbon atoms from a feed comprising a lower alkanoic monoester of said diol which comprises the steps of:
    a. introducing said feed into a distillation zone,
    b. heating said feed in said distillation zone at a temperature within the range of room temperature up to about 280°C. in the presence of a basic disproportionation catalyst which is a weak base or a substance which forms a weak base in situ in the presence of said lower alkanoic ester employed in the amount of 0.001 to 5% by weight based upon the free hydroxyl-group-containing lower alkanoic ester in the feed to convert at least some of said lower alkanoic diester of said diol and to a lower alkanoic diester of said diol, and
    c. recovering said thus-produced diol from said distillation zone, said feed to said reaction zone being produced by partially hydrolyzing with water at least one lower alkanoic diester of said diol.

2. A process as defined in claim 1, wherein said diol is ethylene glycol.

3. A process as defined in claim 1, wherein said monoester and said alkanoic diester are acetates.

4. A process as defined in claim 3, wherein said diol is ethylene glycol.

* * * * *

UNITED STATES PATENT OFFICE
CERTIFICATE OF CORRECTION

PATENT NO. : 3,968,175
DATED : July 6, 1976
INVENTOR(S) : John Kollar

It is certified that error appears in the above–identified patent and that said Letters Patent are hereby corrected as shown below:

Col. 8, line 67, change "99" to -- 90 --.

Signed and Sealed this

Twenty-ninth Day of March 1977

[SEAL]

Attest:

RUTH C. MASON
Attesting Officer

C. MARSHALL DANN
Commissioner of Patents and Trademarks